(12) United States Patent
Slusarewicz

(10) Patent No.: US 6,773,464 B2
(45) Date of Patent: Aug. 10, 2004

(54) HAIR COLORING COMPOSITIONS

(75) Inventor: Pawel Slusarewicz, Irvington, NY (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 209 days.

(21) Appl. No.: 10/117,404

(22) Filed: Apr. 5, 2002

(65) Prior Publication Data

US 2003/0037385 A1 Feb. 27, 2003

(30) Foreign Application Priority Data

Apr. 6, 2001 (GB) .............................................. 0108734

(51) Int. Cl.[7] .................................................. A61K 7/13
(52) U.S. Cl. ...................... 8/405; 8/428; 8/432; 8/493; 8/587; 8/618
(58) Field of Search ........................... 8/405, 428, 432, 8/493, 587, 618

(56) References Cited

U.S. PATENT DOCUMENTS 5,490,980 A * 2/1996 Richardson et al. ....... 424/94.6
5,525,336 A 6/1996 Green et al. ............... 424/94.5

FOREIGN PATENT DOCUMENTS

| WO | 99/36570 | | 7/1999 |
| WO | 00/64405 | | 11/2000 |
| WO | 01/21145 | A1 | 3/2001 |

OTHER PUBLICATIONS

Copending application: Applicant: Slusarewicz, Ser. No.: 10.117,640, Case No.: J3599(C), Filed: Apr. 5, 2002, For: Method of Coloring Hair.

Search Report under Section 17 Application No. GB 0108735.2 dated Oct. 9, 2001.

* cited by examiner

Primary Examiner—Brian P. Mruk
Assistant Examiner—Eisa Elhilo
(74) Attorney, Agent, or Firm—Michael P. Aronson

(57) ABSTRACT

A hair coloring composition or kit of parts comprises: a compound which is capable of acting as a substrate for endogenous transglutaminase in and/or on hair and which comprises a chromophore that is capable of absorbing and/or emitting light in the visible part of the electromagnetic spectrum; and a reducing agent. The composition may be used to coloring hair.

15 Claims, No Drawings

HAIR COLORING COMPOSITIONS

FIELD OF THE INVENTION

This invention relates to hair colouring compositions and methods of colouring hair using the compositions.

BACKGROUND OF THE INVENTION

The cosmetic colouring of hair has been known for many years. Colourants are typically classified as being temporary or permanent. In temporary colouring, the colour can be washed from the hair relatively easily. So-called permanent colouring of hair typically involves the formation of oligomeric or polymeric compounds in and/or on the hair fibre. However, the colouring is not truly permanent in the strict sense of the word because the colourants can still be washed from the hair over longer periods of time.

Therefore, there remains a need for hair colourants which are more resistant to being washed off the hair.

It is known that hair fibres contain certain enzymes in and/or on the fibre. For example, the enzyme transglutaminase has been found to be present in hair fibres. Transglutaminase catalyses the formation of covalent bonds between specific peptide-bound glutamine resides and various primary amino groups of peptide-bound lysines or polyamines, acting as aminic donor substrates.

Transglutaminase can be utilised to attach agents to body tissues, as described in WO99/36570. In the specific systems exemplified in this document, exogenous transgutaminase is used to attach polylysine or polyglutamine to skin or hair. In the only specific example of a system for application to hair, a mousse for thickening hair is described which contains a mucopolysaccharide linked to polyglutamine.

Transglutaminase substrates have been involved in the treatment of hair loss. For example, FR-A-2740331 describes cosmetic compositions for the treatment of hair which contain one or more esters of butyric acid and, optionally, a substrate for transglutaminase.

The use of exogenous transglutaminase in a cosmetic composition for forming a protective layer on the hair, skin or nails, is described in U.S. Pat. No. 5,525,336. The ingredients of the composition cross-link with the outer layer of skin, hair or nails to form the layer.

WO00/64405 describes the use of substrates for a variety of endogenous enzymes that are present in hair fibres, for the delivery of hair benefit agents to the hair. Transglutaminase is one of the endogenous enzymes mentioned in the document.

The present invention is based on the finding of specific systems for colouring hair which may involve the action of endogenous transglutaminase. The systems have the advantage in that the colourant may be covalently bound to the hair fibre and, therefore, more resistant to being removed by washing.

SUMMARY OF THE INVENTION

According to a first aspect of the present invention, there is provided a hair colouring composition or kit of parts comprising: a compound which is capable of acting as a substrate for endogenous transglutaminase in and/or on hair and which comprises a chromophore that is capable of absorbing and/or emitting light in the visible part of the electromagnetic spectrum; and a reducing agent.

In a second aspect, the invention provides a method of colouring hair which comprises treating the hair with a composition according to the first aspect of the invention.

DETAILED DESCRIPTION

The present invention is based on the finding of particularly effective compositions for colouring hair. The compositions contain a compound which can act as a substrate for transglutaminase and a reducing agent. The compound preferably forms a covalent bond to the hair by the action of the endogenous transglutaminase in and/or on the hair.

Compound which is Capable of Acting as a Substrate for Endogenous Transglutaminase The compound which is capable of acting as a substrate for endogenous transglutaminase in and/or on hair and which comprises a chromophore that is capable of absorbing and/or emitting light in the visible part of the electromagnetic spectrum (also referred to herein as the compound) preferably comprises an amino group covalently bonded to the chromophore.

In a preferred embodiment, the compound comprises a group of formula $NH_2$ covalently bonded to the chromophore by a linker group of formula $(CH_2)_n$, wherein n is an integer from 1 to 12, more preferably from 1 to 6, most preferably from 3 to 5. Optionally, the linker group can contain one or more other atoms in the $(CH_2)_n$ chain, such as, for example, O. These compounds are known to be suitable as substrates for transglutaminase. The precise nature of the linker group is not critical, provided that the compound can act as a substrate for transglutaminase. Suitable methods for attaching the amino group to the chromophore via the linker group are well-known in the art. Alternatively, the compound may be synthesised or otherwise obtained with the amino and linker groups already present in the chromophore. The compound may contain one or more than one amino group and/or more than one chromophore.

The compound may be present in the compositions of the invention in solution. Preferably, the solution will be aqueous, containing as solvent from 50 to 100% water. However, other cosmetically acceptable solvents and/or diluents may be present in the solution such as, for example, ethanol and/or other lower alcohols. When the compound is present in solution, it will typically be present in the composition at a concentration of from 0.0001M to 0.01M, although the concentration may fall outside this range and will depend on the product form of the composition.

The nature of the chromophore in the compound can vary widely, provided that, when the compound is bonded to the hair, the hair is coloured by the compound. Therefore, the chromophore can be inorganic (ie, metal ion based) or organic. Preferably, however, the chromophore in the compound is an organic dye. Suitable organic dyes are well-known in the art and may comprise a plurality of ring systems, at least some of which are aromatic, and one or more groups bearing a positive or negative charge.

Although the dye may impart any colour to the hair, the compounds of the invention have been found to be particularly effective at colouring the hair red. A suitable chromophore for colouring the hair red is Texas Red, a commercially available organic dye, although other chromophores may be used instead. Permanent red colouration of hair is difficult to achieve using conventional hair colouring techniques.

The compositions of the invention many comprise a single compound or a mixture of different compounds, for example having the same or different light absorbing and/or emitting properties The Reducing Agent The compositions of the invention comprise a reducing agent. The reducing agent preferably comprises one or more thiol (SH) groups. Compounds containing thiol groups are known in other applications to be cosmetically acceptable for application to the hair.

Suitable reducing agents include, for example, compounds containing from 1 to 6 carbon atoms and one or more other functional groups such as hydroxyl and carboxylate, eg, dithiothreitol, thioglycolate and mixtures thereof.

A non-exausitive list of reducing agents is as follows: Mercapto-carboxylic Acids (e.g. 2-mercaptopropionic acid, 3-mercaptopropionic acid, mercaptosuccinic acid, thioglycolic acid, ammonium thioglycollate, sodium thioglycollate, L-cysteine, Di-mercapto-adipic acid); Mercapto-amines (e.g. L-cysteine ethyl ester, L-cysteine methyl ester, N-acetyl-L-cysteine, cysteamine); Mercapto-amides (e.g. thioglycolamide, N-hydroxyethyl mercapto-acetamide, N-methyl mercapto acetamide, 2-mercapto-propionamide); Sulphites (e.g. ammonium bisulphite, sodium bisulphite, ammonium sulphite, sodium sulphite); hydroxides (e.g. guanidine hydroxide, sodium hydroxide); Alcohols and Diols (e.g. resorcinol, thioglycerol, glycerol monothioglycollate, glycol thioglycolate); Di-thio compounds (e.g. dihydrolipoic acid, sodium dihydrolipoate, dithiothreitol, 1,3-dithiopropanol); Others (e.g. lithium chloride, tris(hydroxymethyl)phosphine, cuprammonium hydroxide, thioglycolic hydrazide, 2-mercapto-ethanesulphonic acid, homocysteine thiolactone, polythiol polymers, salts of hydrogen sulphide, amines in alkaline solution, salts of hydrogen cyanide, borohydride, dithionite, ester salts of sulphoxylate).

The reducing agent is typically present in the compositions of the invention in solution. Preferably, the solution will be aqueous, containing as solvent from 50 to 100% water. However, other cosmetically acceptable solvents and/or diluents may be present in the solution such as, for example, ethanol and/or other lower alcohols. When the reducing agent is in solution, it is preferably present in the composition in an amount such that the molar ratio of the reducing agent to the compound is in the range of from 10 1 to 1:1.

Compositions of the Invention

Compositions of the invention preferably have a pH of from about 7.5 to about 9.5, more preferably from about 8 to about 9. It has been found that compositions having pH values within this range are particularly effective at colouring hair. The pH can be maintained within this range by the use of suitable buffering agents. Suitable buffering agents are conventional in the art.

Hair Colouring Agents

The hair colouring compositions of the present invention optionally additionally include one or more conventional hair colouring agents. Hair colouring agents suitable for use in the compositions of the present invention include non-oxidative dyes. Such hair colouring agents may be used with the compositions of the present invention to formulate compositions which have suitable colours and which retain the colour over a period of time.

Non-oxidative dyes include direct dyes, semi-permanent, temporary and other dyes. Various types of non-oxidative dyes are well known in the art.

Natural dyes and vegetable dyes may also be included in the colouring compositions of the present invention. Examples include henna, camomile, indigo, logwood and walnut hull extract.

Temporary hair dyes, or hair colouring rinses, are generally comprised of dye molecules which are too large to diffuse into the hair shaft and which act on the exterior of the hair. They are usually applied via a leave-in procedure in which the dye solution is allowed to dry on the hair surface.

Semi-permanent hair dyes are generally larger than permanent (oxidative) dyes. Typically, semi-permanent dyes act in a similar manner to oxidative dyes in that they have the potential to diffuse into the hair shaft. However, semi-permanent dyes are generally smaller in size than the aforementioned conjugated oxidative dye molecules and as such are pre-disposed to gradual diffusion out of the hair again. Simple hair washing and cleaning action will encourage this process. Suitable semi-permanent dyes for use in the compositions of the present invention include HC Blue 2, HC Yellow 4, HC Red 3, Disperse Violet 4, Disperse Black 9, HC Blue 7, HC Yellow 2, Disperse Blue 3, Disperse violet I and mixtures thereof.

Direct dyes, such as nitro dyes do not require oxidation to dye the hair. They are usually applied to the hair in a base formulation which includes surfactant material. Suitable direct dyes include derivatives of nitroamino benzene, nitro aryl amines or azo dyes.

Optional Materials and Cosmetic Adjunct

Besides the actives, the compositions of the present invention may also contain other ingredients conventionally used in the art such as diluents, sequestrants, thickeners, carriers, surfactants (anionic, cationic, nonionic, amphoteric, zwitterionic and mixtures thereof), antioxidants, proteins, polypeptides, preservatives, moisturising agents, solvents, perfumes, enzymes, polymers and conditioners.

The compositions of the invention may comprise a source of calcium ions (for example a soluble inorganic calcium salt). Calcium ions may assist the action of the transglutaminase enzyme. However, a source of calcium ions is not essential because, due to the presence of calcium from other sources (for example in local water), sufficient calcium ions may already be present.

The compositions may contain exogenous transglutaminase in order to assist in binding of the hair fibre to the compound. However, the invention can work effectively without exogenous transglutaminase, relying solely on transglutaminase in and/or on the hair. Therefore, the compositions of the invention are preferably free or substantially free of exogenous transglutaminase.

Compositions of the invention may optionally contain hair penetration agents. Hair penetration agents assist the penetration of molecules into the hair fibre and are conventionally used for this purpose. Suitable hair penetration agents include, for example, compounds comprising amino and/or amide groups such as urea and guanidine, for example. The reducing agent which is used in the compositions of the invention may also act as a hair penetration agent.

Product Form

The compositions according to the present invention may be presented in the form of a kit of parts comprising a number of separate compartments containing the various ingredients of the final composition for mixing by the user immediately prior to application to the hair. The kit may comprise multiple containers or a single container having multiple compartments.

One component of the kit comprises a compound which is capable of acting as a substrate for endogenous transglutaminase in and/or on hair and which comprises a chromophore that is capable of absorbing and/or emitting light in the visible part of the electromagnetic spectrum, individually packaged. A further kit component comprises an individually packaged reducing agent. Optional ingredients may be incorporated into either component, generally depending on their stability in the different components which can be readily determined by the skilled person.

The compartmentalised ingredients of the composition are generally mixed by the user immediately prior to application to the hair. Thus, the compositions of the invention can be formed by mixing together the components of the kit of parts. Reference herein to the properties of compositions means the compositions obtained after mixing the components, when the invention is a kit of parts.

Method of Use

The compositions of the present invention may be used to colour hair. The compositions may be intended solely for colouring hair for use in a method dedicated to hair colouring. In such methods, the colouring compositions herein are applied to the hair for periods of from 1 minute to 90 minutes depending upon the degree of colouring required. A preferred time is between 5 minutes and 30 minutes. Hair is typically rinsed, optionally washed, and dried after such treatment. Elevated temperatures (eg, from 35 to 50° C.) may be employed at any stage of the treatment process.

The method of the invention may be applied to unpigmented hair eg, white or grey hair. The method may also be used to colour hair which is naturally pigmented or otherwise coloured (eg, by an earlier dyeing step). Transglutaminase has been found to be present in pigmented and unpigmented hair.

As an alternative to dedicated hair colouring, the compositions of the invention may be products which are regularly applied to the hair for cleaning, conditioning or other purposes. Thus, the compositions of the invention may be formulated as shampoo or conditioner compositions. By formulating the compositions as shampoo or conditioner products, the hair may be coloured gradually each time the composition is used. Compositions for regular use may be used as a supplementary treatment for hair coloured in a specific hair colouring step.

Shampoo and/or Conditioner Compositions

Shampoo compositions of the invention comprise at least one surfactant which provides a deterging benefit. The deterging surfactant is preferably selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts.

The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Further nonionic surfactants which can be included in shampoos for the invention are the alkyl polyglycosides (APGs). Typically, the APG is one which comprises an alkyl group connected (optionally via a bridging group) to a block of one or more glycosyl groups. Preferred APGs are defined by the following formula:

RO—(G)$_n$ wherein R is a branched or straight chain alkyl group which may be saturated or unsaturated and G is a saccharide group. Suitable alkyl polyglycosides for use in the invention are commercially available and include for example those materials identified as: Oramix NS10 ex Seppic; Plantaren 1200 and Plantaren 2000 ex Henkel.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactants are present in shampoo compositions of the invention in an amount of from 0.1 to 50% by weight of the composition, preferably from 0.5 to 30% by weight.

Compositions in accordance with the invention may also take the form of hair conditioning compositions, which may be rinse off or leave-on hair conditioning compositions or so-called 2 in 1 compositions containing shampoo and conditioner. The conditioning compositions preferably comprise one or more cationic surfactants. The use of cationic surfactants is especially preferred, because these ingredients are capable of providing conditioning benefits to hair.

Examples of cationic surfactants include: quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethyl-ammonium hydroxide, hexadecyltrimethylammonium hydroxide, cetyltrimethylammonium hydroxide, octyldimethylbenzylammonium hydroxide, decyldimethyl-benzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof, e.g., chlorides, Cetylpyridinium hydroxide or salts thereof, e.g., chloride ,Quaternium-5, Quaternium-31, Quaternium-18, and mixtures thereof.

In hair conditioning compositions according to the invention, the level of cationic surfactant is preferably from 0.01 to 10%, more preferably 0.05 to 5%, most preferably 0.1 to 2% by weight of the composition.

Hair conditioning compositions of the invention may also contain one or more conditioning agents, preferably selected from silicones, protein hydrolysates and quaternised protein hydrolysates and other materials which are known in the art as having desirable hair conditioning properties.

Silicones are the most preferred conditioning agents.

Suitable silicones include volatile and non-volatile silicones, such as for example polyalkylsiloxanes, polyalkylaryl siloxanes, siloxane gums and resins, cyclomethicones, aminofunctional silicones, quaternary silicones and mixtures thereof. Silicone oil is a particularly preferred conditioning agent for hair. The silicone may be in the form of a low viscosity oil which may contain a high viscosity oil or gum in solution.

Alternatively, the high viscosity material may be in the form of an emulsion in water. The emulsion may be of high viscosity oil or of a solution of gum in a lower viscosity oil. The particle size of the oil phase may be anywhere in the range from 30 nanometres to up to 20 microns average size.

The silicone oil may suitably be a polydimethylsiloxane with an average particle size of less than 20 microns and preferably less than 2 microns. Small particle size enables a more uniform distribution of silicone conditioning agent for the same concentration of silicone in the composition. Advantageously, a silicone with a viscosity in the range 1–20 million cst is used. The silicone can be cross-linked.

Preferred silicones include polydimethylsiloxanes (of CTFA designation dimethicone) and hydroxylated polydimethylsiloxanes (of CTFA designation dimethiconol).

Silicones of the above types are widely available commercially, for example as DC-1784 and DCX2-1391, both ex Dow Corning.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

In accordance with the invention, the hair shampoo and/or conditioner composition may also comprise a polymeric water-soluble cationic polymer as a conditioning agent.

The cationic polymer may be present at levels of from 0.01 to 5%, preferably from about 0.05 to 1%, more preferably from about 0.08% to about 0.5% by weight.

Synthetic or naturally derived polymers having a quaternised nitrogen atom are useful. The molecular weight of the polymer will generally be between 5 000 and 10 000 000, typically at least 10 000 and preferably in the range 100 000 to about 2 000 000.

Representative synthetic quaternised polymers include, for example: cationic copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA". as Polyquaternium-16); copolymers of 1-vinyl-2-pyrrolidine and dimethylaminoethyl methacrylate (referred to in the industry by CTFA as Polyquaternium-11); cationic diallyl quaternary ammonium-containing polymers including, for example, dimethyldiallylammonium chloride homopolymer (referred to in the industry (CTFA) as Polyquaternium 6); mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in WO95/22311.

Representative naturally-derived quaternised polymers include quaternised cellulosic compounds and cationic guar gum derivatives, such as guar hydroxypropyltrimonium chloride. Examples are JAGUAR C-13S, JAGUAR C-15, and JAGUAR-C17, commercially available from Meyhall in their JAGUAR (trademark) series.

Suitable cationic polyacrylamides are described in WO 95/22311 whose contents are incorporated herein by reference.

The compositions may further comprise from 0.1 to 5% of a suspending agent. Examples are polyacrylic acids, cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearates, alkanolamides of fatty acids having from 16 to 22 carbon atoms and mixtures thereof. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark. A further suitable suspending agent is dihydrogenated tallow phthalic acid amide (available from Stepan under the trademark Stepan TAB-2).

Suitable cross linked polymers of acrylic acid and acrylate esters are Pemulen TR1 or Pemulen TR2. A suitable heteropolysaccharide gum is xanthan gum, for example that available as Kelzan mu.

Another ingredient that may advantageously be incorporated into shampoo and/or conditioning compositions of the invention is a fatty alcohol material. The use of these materials is especially preferred in conditioning compositions of the invention, in particular conditioning compositions which comprise one or more cationic surfactant materials. The combined use of fatty alcohol materials and cationic surfactants in conditioning compositions is believed to be especially advantageous, because this leads to the formation of a lamellar phase, wherein the cationic surfactant is dispersed.

Preferred fatty alcohols comprise from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invention.

The level of fatty alcohol materials is conveniently from 0.01 to 10%, preferably from 0.1 to 5% by weight of the composition. The weight ratio of cationic surfactant to fatty alcohol is preferably from 10:1 to 1:10, more preferably from 4:1 to 1:8, most preferably from 1:1 to 1:4.

A further ingredient that may be desirably included in the shampoo and/or conditioning compositions is a pearlescent material. Suitable pearlescent materials include ethylene glycol distearate, ethylene glycol monostearate, guanine and titanium dioxide coated micas, bismith oxychloride, and stearic monoethanol amide. The level of pearlescent material present in the composition is generally 0.1% to 5%, preferably from 0.3% to 3% by weight of the composition.

The shampoo and/or conditioner compositions of the invention are preferably aqueous based. The compositions suitably comprise water in amount of from about 20 to about 99% by weight of the total composition.

The invention will now be described, by way of non-limiting example only, with reference to the following examples. In the examples and throughout this specification, all references to percentages are to percentages by weight unless indicated otherwise.

EXAMPLES

Materials and Methods

In each experiment, unpigmented hair fibres were used as clippings of 2–5 mm in length. Hair fibres from a greying male were obtained and the unpigmented hairs manually separated from the pigmented. Only unpigmented hairs were used in these studies.

Observations of Penetration and Incorporation of Dye into Hair

Aliquots of approximately 5 mg of dry unpigmented hair fibres with an average length of 5 mm were placed into Eppendorf tubes. 50 $\mu$l of assay mixture containing 100 mM Tris. HCl pH 8.5, 5 mM $CaCl_2$, 10 mM DTT, 0.5% (w/v) Triton X-100 was added to each sample. The assay mixture was made up fresh each time from 1M stocks of Tris pH8.5, CaCl$_2$ (both stored at room temperature) and DTT (stored at −20° C.) and 10% Triton X-100 (stored at 4° C.). 50 µl of 2 or 4 mM Texas Red-cadaverine (Molecular Probes) (TRC; 10 mM stock in DMSO stored at −20° C.) was then added to each sample to give a final concentration of 2 mM of TRC.

After 10 min of incubation at room temperature, the assay mixture was removed and the fibres were rinsed briefly in 1 ml of 0.1% Triton X-100. Hair fibres were recovered by centrifugation at 13,000 rpm for 10 seconds and the wash solution was removed. The fibres were then spread over the inner surface of the tube and left to dry at room temperature for 1 hour. Following the fibre drying step, 50 µl of water was added to the bottom of each tube to maintain humidity, and the tubes were sealed and incubated at room temperature for 24 hours from the time the assay solutions were applied. The aim of this 24-hour post incubation was to allow an additional incorporation of TRC within the fibre.

Once this incubation had been completed, fibres were washed three times in 1 ml of 0.1% Triton-X100 for 20 min at 95° C. (total wash time: 60 min). In some experiments one set of samples was not washed in order to quantitate the penetration of TRC within the fibre. At this step of the experiment photographs were taken in order to compare the intensity of the colour change by human eye between the different conditions tested.

Fibres were then solubilised by the addition of 1 ml of 90% soluene and incubated at room temperature until complete solubilization had occurred (48 hours) in parallel with a standard curve of TRC (0.1–5 µM, final concentration). The penetration or incorporation of TRC into hair fibres was measured by fluorimetry at 580 nm excitation and 598 nm emission after dilution of the samples 2-fold with 90% soluene.

Example 1

TRC (2 mM final) was applied for 10 minutes from: (i) the assay mixture described above; (ii) water; (iii) Tris (100 mM final); (iv) Triton X-100 (0.5% final); (v) CaCl$_2$ (5 mM final); and (vi) DTT (10 mM). Fibres were then rapidly rinsed and incubated at room temperature for 24 hours.

Penetration and incorporation of TRC into the fibres were measured by fluorimetry after hair solubilisation.

The results are shown in Table 1:

TABLE 1

|  | Incorporation (pmol/mg) | Penetration (pml/mg) |
| --- | --- | --- |
| Assay Mixture | 730 | 11,000 |
| Water | 40 | 3,500 |
| Tris | 70 | 5,500 |
| Triton X-100 | 10 | 1,500 |
| CaCl$_2$ | 10 | 1,500 |
| DTT | 60 | 3,750 |

Example 2

The effect of pH on penetration and incorporation of TRC were also studied. TRC (2 mM final) was applied for 10 minutes from: (i) assay mixture as described above; (ii) Tris (100 mM final); (iii) Tris plus 10 mM DTT; or(iv) water. Fibres were then rapidly rinsed and incubated at room temperature for 24 hours. Penetration and incorporation were measured by fluorimetry after hair solubilisation.

The results are shown in Table 2:

TABLE 2

|  | Incorporation (pmol/mg) | Penetration (pml/mg) |
| --- | --- | --- |
| Assay Mixture | 450 | 7,500 |
| Tris | 120 | 4,000 |
| Tris/DTT | 1,300 | 19,000 |
| Water | 220 | 3,500 |

The results show that Tris pH 8.5 and DTT display a synergistic effect with respect to both penetration and incorporation of TRC. Indeed, both penetration and incorporation appeared to be greater from the Tris/DTT than from the assay mixture itself. This may be due to inhibitor effects of the other assay mixture components (TritonX-100, CaCl$_2$) which under certain circumstances were shown to retard TRC penetration.

Taken together these data provide evidence the pH plays an important role in the penetration of TRC and its incorporation. Furthermore the presence of a reducing agent gives a synergistic effect with regard to both penetration and incorporation.

Example 3

The following is an example of a shampoo composition according to the invention.

| Ingredient Chemical Name | Example 3 a.i. weight % |
| --- | --- |
| SLES 2EO | 14 |
| Cocoamidopropylbetaine | 2 |
| Guar hydroxypropyltrimonium chloride | 0.1 |
| Dimethiconol | 1 |
| Crosslinked polyacrylic acid | 0.4 |
| Texas Red-cadaverine | 0.4 |
| Dithiothreitol | 0.2 |
| Mica + titanium dioxide | 0.2 |
| Sodium benzoate | 0.5 |
| Water | to 100 |

Example 4

The following is an example of a rinse-off conditioning composition according to the invention.

| Ingredient Chemical Name | Example 4 weight % |
| --- | --- |
| Soft water | q.s. to 100 |
| Citric acid (50% aqueous) | 0.185 |
| Stearamidopropyldimethylamine | 0.5 |
| Propylene glycol | 0.5 |
| Dicetyldimonium chloride/PG | 2.1 |
| Texas Red-cadaverine | 0.4 |
| Dithiothreitol | 0.2 |
| Stearyl alcohol and ceteareth-20 blend | 1.0 |
| Cetyl alcohol | 3.25 |
| Disodium EDTA | 0.1 |
| Methylchloroisothiazoline/methylisothiazoline | 0.05 |

-continued

| Ingredient Chemical Name | Example 4 weight % |
|---|---|
| DMDM hydantoin | 0.1 |
| Potassium hydroxide (50% aqueous) | 0.033 |
| Fragrance | 0.2 |
| Potassium chloride | 0.1 |

What is claimed is:

1. A hair colouring composition comprising: a compound which is capable of acting as a substrate for endogenous transglutaminase in and/or on hair and which comprises a chromophore that is capable of absorbing and/or emitting light in the visible part of the electromagnetic spectrum; and a reducing agent comprising one or more thiol groups, wherein the said compound forms a covalent bond to the hair by the action of the endogenous transglutaminase.

2. A composition as claimed in claim 1, wherein the compound comprises an amino group covalently bonded to the chromophore.

3. A composition as claimed in claim 1, wherein the compound comprises a group of formula $NH_2$ covalently bonded to the chromophore by a linker group of formula $(CH_2)_n$, wherein n is an integer from 1 to 6.

4. A composition as claimed in claim 1, wherein the compound is in solution and is present in the composition at a concentration of from 0.0001M to 0.01M.

5. A composition as claimed in claim 1, wherein the reducing agent comprises dithiothreitol, thioglycolate or a mixture thereof.

6. A composition as claimed in claim 1, wherein the reducing agent is in solution and is present in the composition in an amount such that the molar ratio of the reducing agent to the compound is in the range of from 10:1 to 1:1.

7. A composition as claimed in claim 1 which has a pH of from 7.5 to 9.5.

8. A composition as claimed in claim 7 which has a pH of from 8 to 9.

9. A composition as claimed in claim 1, wherein the chromophore is an organic dye.

10. A composition as claimed in claim 9, wherein the dye colours hair red.

11. A composition as claimed in claim 1, which further comprises a fragrance or perfume.

12. A composition as claimed in claim 1, which further comprises one or more surfactants.

13. A composition as claimed in claim 1, which further comprises calcium ions.

14. A composition as claimed in claim 1, which comprises a hair penetration agent.

15. A composition as claimed in claim 1, which further comprises a cosmetically acceptable diluent or carrier.

* * * * *